US008540691B2

(12) United States Patent
Hasegawa et al.

(10) Patent No.: US 8,540,691 B2

(45) Date of Patent: Sep. 24, 2013

(54) DRUG SOLUTION TRANSFERRING DEVICE

(75) Inventors: Mitsuru Hasegawa, Osaka (JP); Takeshi Ohguro, Osaka (JP)

(73) Assignee: Nipro Corporation, Osaka (JP)

( * ) Notice: Subject to any disclaimer, the term of this patent is extended or adjusted under 35 U.S.C. 154(b) by 125 days.

(21) Appl. No.: 12/829,416

(22) Filed: Jul. 2, 2010

(65) Prior Publication Data

US 2011/0004185 A1 Jan. 6, 2011

(30) Foreign Application Priority Data

Jul. 3, 2009 (JP) ................................ 2009-158910

(51) Int. Cl.

| | |
|---|---|
| ***A61M 5/32*** | (2006.01) |
| *A61M 5/24* | (2006.01) |
| *B65D 51/00* | (2006.01) |
| *B65B 1/04* | (2006.01) |

(52) U.S. Cl.

USPC ............ 604/411; 604/88; 604/195; 604/200; 604/283; 604/412; 215/247; 215/253; 141/329

(58) Field of Classification Search

USPC .................. 604/411, 88, 195, 200, 283, 412; 215/247, 253; 141/329

See application file for complete search history.

(56) References Cited

U.S. PATENT DOCUMENTS

| | | | | |
|---|---|---|---|---|
| 4,564,054 | A * | 1/1986 | Gustavsson | 141/329 |
| 4,927,423 | A * | 5/1990 | Malmborg | 604/88 |
| 5,176,673 | A | 1/1993 | Marrucchi | |
| 5,338,311 | A * | 8/1994 | Mahurkar | 604/195 |
| 5,478,337 | A * | 12/1995 | Okamoto et al. | 604/413 |
| 5,545,139 | A | 8/1996 | Kriesel | |
| 5,924,584 | A * | 7/1999 | Hellstrom et al. | 215/247 |
| 6,139,534 | A * | 10/2000 | Niedospial et al. | 604/411 |
| 7,374,558 | B2 * | 5/2008 | Kirchhofer | 604/200 |
| 2007/0023430 | A1 | 2/2007 | Seher et al. | |
| 2008/0251490 | A1 * | 10/2008 | Livingston et al. | 215/253 |
| 2009/0326506 | A1 | 12/2009 | Hasegawa et al. | |

FOREIGN PATENT DOCUMENTS

| | | | |
|---|---|---|---|
| CA | 1 215 945 | A1 | 12/1986 |
| CN | 87 1 06419 | A | 3/1988 |
| EP | 0 314 602 | A2 | 5/1989 |
| JP | 04-075542 | U | 7/1992 |
| JP | 7-213585 | A | 8/1995 |
| JP | 2001-158449 | A | 6/2001 |
| JP | 2001-187110 | A | 7/2001 |
| JP | 2001-321416 | A | 11/2001 |

(Continued)

*Primary Examiner* — Jacqueline F Stephens
*Assistant Examiner* — Andrew J Mensh
(74) *Attorney, Agent, or Firm* — Birch, Stewart, Kolasch & Birch, LLP

(57) ABSTRACT

A drug solution transferring device that can suppress dispersion of a toxic drug solution to a surrounding environment is provided. The drug solution transferring device includes a barrel provided with an opening, and a connection tool for connection to the barrel. The barrel includes an elastic member for closing the opening. The elastic member is formed of a plurality of membranes overlaid together. The membrane has a projection projecting into the barrel. The connection tool includes a first needle having a sharp tip end. The first needle has a liquid hole extending in an extending direction of the first needle. When the needle penetrates through the projection of the membrane, an inside and an outside of the barrel are in communication with each other through the liquid hole to allow transference of the drug solution between the barrel and the connection tool.

7 Claims, 9 Drawing Sheets

(56) References Cited

FOREIGN PATENT DOCUMENTS

| | | | |
|---|---|---|---|
| JP | 2002-177365 | A | 6/2002 |
| JP | 2002-272843 | A | 9/2002 |
| JP | 2003-267407 | A | 9/2003 |
| JP | 2007-502242 | A | 2/2007 |
| JP | 2008-307237 | A | 12/2008 |
| WO | WO 95/05863 | A1 | 3/1995 |
| WO | WO 03/030809 | A1 | 4/2003 |
| WO | WO 03/086529 | A1 | 10/2003 |
| WO | WO 03/086530 | A1 | 10/2003 |
| WO | WO 2005/041846 | A2 | 5/2005 |
| WO | WO 2007/148708 | A1 | 12/2007 |

* cited by examiner

DRUG SOLUTION TRANSFERRING DEVICE

This nonprovisional application is based on Japanese Patent Application No. 2009-158910 filed on Jul. 3, 2009 with the Japan Patent Office, the entire contents of which are hereby incorporated by reference.

BACKGROUND OF THE INVENTION

1. Field of the Invention

The present invention relates to a drug solution transferring device, and particularly to a drug solution transferring device for transferring a toxic drug solution.

2. Description of the Background Art

In a medical institution such as a hospital, conventionally, a dry preparation such as a powdery drug or a freeze-dried drug, which is held in a drug container such as a vial, is dissolved in a solvent for use, and a resultant drug solution is used as an infusion for drip injection. Such a drug will lose its efficacy when it is kept in a state of a drug solution and, consequently, can not be stored in the state of the drug solution. An injection syringe filled with the solvent is connected to the drug container to inject the solvent into the drug container so that the dry preparation in the drug container is dissolved.

In process of dissolving and preparing a toxic drug such as anti-cancer drug, an injection syringe may be removed in such a state that a pressure is applied to a connection portion of the injection syringe or a hydraulic pressure in the infusion container is applied thereto. In this case, a splash or spill of the drug solution may occur at the connection portion even when the pressure is small. When the toxic drug splashes or spills, or when it dries thereafter, an aerosol generates and floats so that the toxic drug is exposed in an ambient environment for a long period of time, resulting in a problem that the toxic drug may exert an adverse influence on health of medical staffs and patients.

Accordingly, there has been proposed a drug solution preparing kit that does not cause the liquid leakage such as a splash and dispersion of an aerosol during preparation of a drug solution (e.g., International Publication No. WO2007/148708).

According to the drug solution preparing kit in International Publication No. WO2007/148708, when a drug that is already prepared is drawn into a barrel and then the barrel is separated from the transfusing tool, a sealing member provided at an end opening of the barrel closes to prevent leakage of the prepared drug. When the prepared drug solution is drawn into the barrel, the pressure in the system becomes lower than an ambient pressure. Therefore, even when a splash or aerosol spouts, the splash or the aerosol occurs inside the vial, and are prevented from external dispersing from the system.

According to the drug solution preparing kit in International Publication No. WO2007/148708, a vial is attached to a vial attaching unit of a transfusing tool, and a first needle covered with a covering member is stuck into an elastic film of the barrel to attach the barrel to the barrel attaching unit. In this state, the drug is dissolved and prepared in the vial, and subsequently a nominal volume of drug solution is drawn into the barrel. Then, the transfusing tool is removed from the barrel.

When the first needle is pulled out from the elastic film of the barrel, a residual toxic drug adhering to the first needle may adhere to a portion near a tip end of the covering member. The toxic drug adhering to the covering member may change into an aerosol. The aerosol thus generated floats, and is partially dried during floating to change into smaller particles of a high drug concentration. This results in a problem that the medical staffs and the patients are exposed to the toxic drug.

SUMMARY OF THE INVENTION

A primary object of the invention is to provide a drug solution transferring device that can suppress environmental dispersion of a toxic drug solution during transference of the drug solution.

A drug solution transferring device according to the invention includes a drug solution container provided with an opening; and a connection tool for connection to the drug solution container. The drug solution container includes an elastic member for closing the opening. The elastic member is formed of a plurality of membranes overlaid together. The membrane has a projection projecting into the drug solution container. The connection tool includes a needle having a sharp tip end. The needle has a liquid hole extending in an extending direction of the needle. When the needle penetrates through the projection of the membrane, an inside and an outside of the drug solution container are communicated with each other through the liquid hole to allow transference of the drug solution between the drug solution container and the connection tool.

Preferably, in the above drug solution transferring device, the projection has a hemispherical form.

Preferably, in the above drug solution transferring device, the connection tool includes a covering unit, a cylindrical portion and an elastic film. The covering unit covers the needle and is elastically deformable. The cylindrical portion has a hollow form, and accommodates the needle and the covering unit. The elastic film is arranged at an end portion of the cylindrical portion near the tip end of the needle, and covers the end portion. The elastic film has a slit opening.

Preferably, in the above drug solution transferring device, the drug solution container includes a pipe portion projecting toward an outside of the drug solution container. The elastic member is arranged to close a hollow in the pipe portion. The pipe portion has an outer diameter smaller than an inner diameter of the cylindrical portion for allowing insertion of the pipe portion through the slit opening into the cylindrical portion. The needle is stuck into the membrane by inserting the pipe portion into the cylindrical portion.

The drug solution transferring device according to the invention can suppress dispersion of a toxic drug solution to a surrounding environment during transference of the drug solution.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Embodiments of the invention will now be described with reference to the drawings. In the following description, the same or corresponding portions bear the same reference numbers, and description thereof is not repeated.

In the embodiments described below, each of components is not essential in the invention, unless otherwise specified. In the embodiments described below, numbers, amounts and the like are merely examples, unless otherwise specified, and the scope of the invention is not restricted to such numbers, amounts and the like.

First Embodiment

Figure 1:
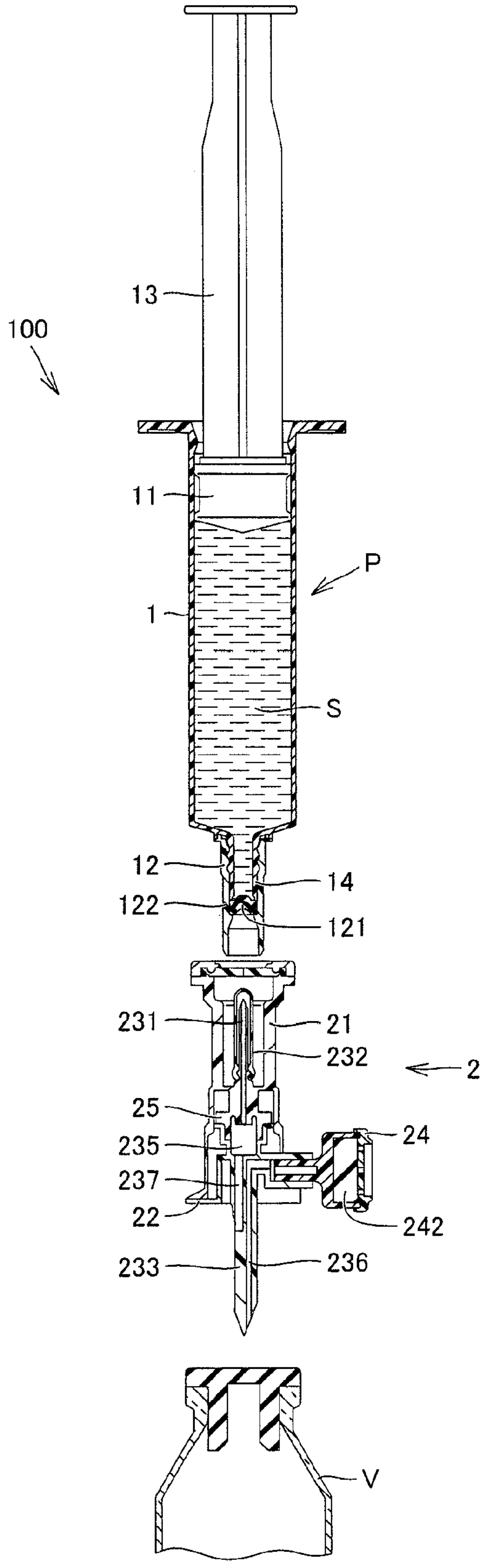
FIG. 1 is a cross section showing a structure of a drug solution transferring device according to a first embodiment of the invention.

As shown in FIG. 1, a drug solution transferring device 100 according to a first embodiment includes a pre-filled syringe P filled with a solvent S and a connection tool 2 connected to pre-filled syringe P. Connection tool 2 is attached to pre-filled syringe P and a vial V containing the drug so that inner spaces thereof are communicated with each other. Owing to the communication between pre-filled syringe P and vial V through connection tool 2, the drug contained in vial V is mixed and dissolved in a solvent S to prepare the drug solution.

Figure 2:
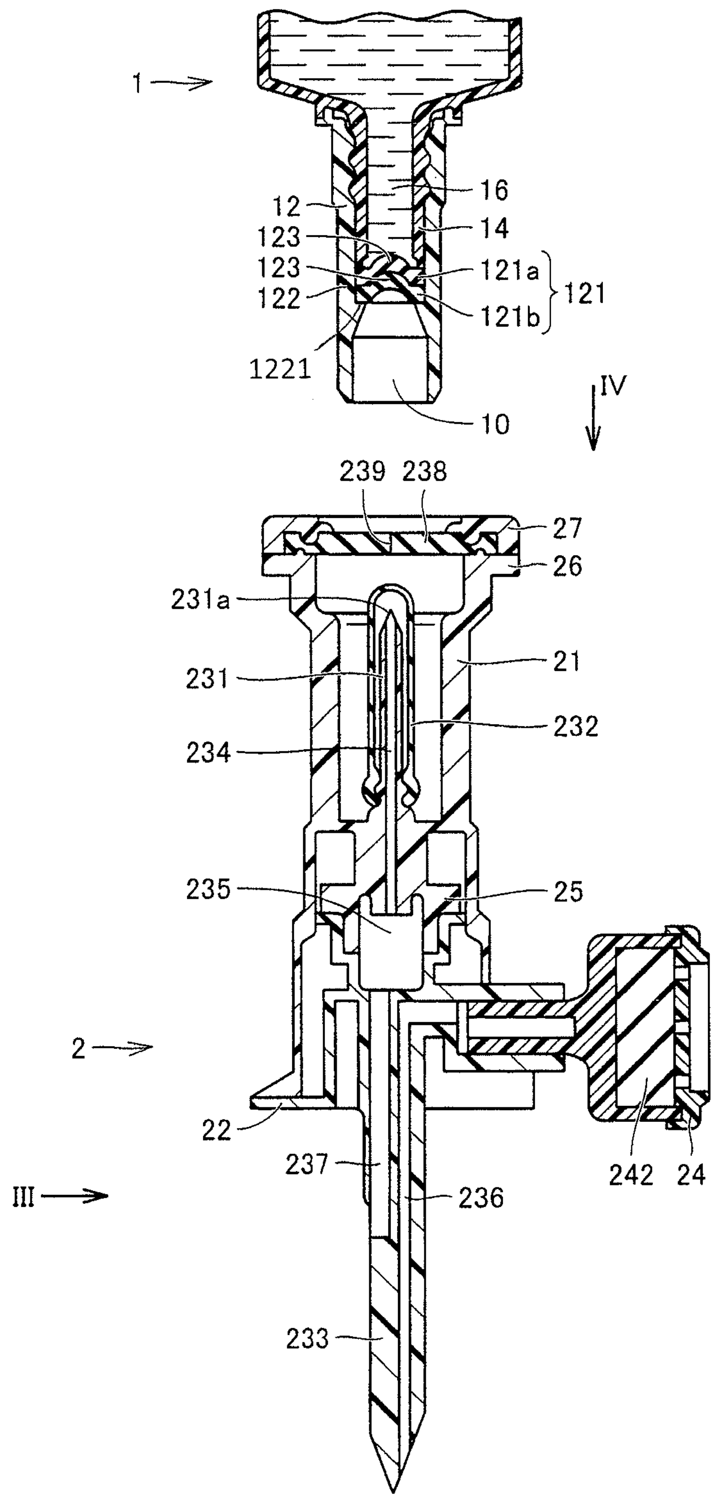
FIG. 2 is a fragmentary cross section showing, on an enlarge scale, the drug solution transferring device shown in FIG. 1.

Pre-filled syringe P has a cylindrical barrel 1 which is an example of a drug solution container and is open at its opposite ends. Barrel 1 has a nozzle 14 of a small diameter at its tip end. A sealing member 12 is attached to nozzle 14. Sealing member 12 includes an elastic member 121 and a caulking member 122. Elastic member 121 is liquid-tightly attached to nozzle 14 by caulking member 122. Caulking member 122 is unremovable from nozzle 14. As shown in FIG. 2, the caulking member 122 includes a step 1221 formed on an inner periphery of the caulking member, and the elastic member 121 is clamped between the step 1221 and the opening of the drug solution container to seal the opening of the drug solution container.

Nozzle 14 and caulking member 122 form a hollow pipe portion. Caulking member 122 is fixed to an outer periphery of nozzle 14 to form the pipe portion of an integrated structure together with nozzle 14. Barrel 1 includes a pipe portion projecting outward from barrel 1. The pipe portion is internally provided with a space 16. An elastic member 121 is arranged to close space 16 in the pipe portion. The pipe portion is provided at its tip end portion (i.e., a tip end portion of caulking member 122) with an opening 10 forming an end opening of barrel 1. Elastic member 121 closes opening 10.

Elastic member 121 is formed of a plurality of membranes 121*a* and 121*b* overlaid together. A surface of membrane 121*a* near opening 10 and a surface of membrane 121*b* near the inside of barrel 1 are in intimate contact with each other. Elastic member 121 is formed of membranes 121*a* and 121*b* that are overlaid together to keep intimate contact without a space and thereby form an integrated elastic member.

Each of membranes 121*a* and 121*b* has a projection 123 projecting into barrel 1. Projections 123 thus formed concave the surface of elastic member 121 opposed to opening 10. The respective projections 123 formed at membranes 121*a* and 121*b* have the same form so that the surfaces of membranes 121*a* and 121*b* can be entirely in intimate contact. As shown in FIG. 2, projection 123 has a hemispherical form.

A gasket 11 is liquid-tightly and slidably fitted into barrel 1 through the rear end opening of barrel 1. Gasket 11 is coupled to a plunger 13. A space defined by barrel 1, sealing member 12 and gasket 11 is filled with solvent S.

Connection tool 2 is used for establishing communicative connection between pre-filled syringe P and vial V, and includes a partition wall 25 as well as a barrel attaching unit 21 and a vial attaching unit 22 which are provided on opposite surfaces of partition wall 25, respectively. Barrel attaching unit 21 has a hollow cylindrical form. Connection tool 2 includes barrel attaching unit 21 as an example of a cylindrical portion.

Barrel attaching unit 21 accommodates a first needle 231 that can penetrate through elastic member 121 of sealing member 12 of pre-filled syringe P when connection tool 2 is attached to pre-filled syringe P. First needle 231 is an example of a needle unit having a sharp tip end 231*a*. First needle 231 has a liquid hole 234 extending in an extending direction (longitudinal direction in FIG. 2) of first needle 231.

As shown in FIG. 2, liquid hole 234 is open at tip end 231*a* of first needle 231. First needle 231 is covered with a rubber cap 232 that is an example of a covering unit covering first needle 231. Rubber cap 232 is elastically deformable. Barrel attaching unit 21 accommodates first needle 231 and rubber cap 232.

Vial attaching unit 22 has a second needle 233 that can penetrate through a plug of vial V when vial V is attached to connection tool 2. Second needle 233 is coaxial with first needle 231. Second needle 233 has a liquid hole 237 extending in the extending direction of second needle 233. Liquid holes 234 and 237 formed in first and second needles 231 and 233, respectively, are communicated with each other via a communication space 235.

Figure 3:
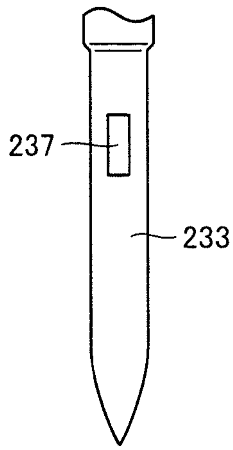
FIG. 3 is a schematic view of a second needle viewed in a direction of an arrow III in FIG. 2.

As shown in FIGS. 2 and 3, the end of liquid hole 237 at the tip end of second needle 233 is open at the outer peripheral surface of second needle 233.

Connection tool 2 further includes a port 24. An aerosol filter 242 that can catch aerosol is arranged in port 24. Second needle 233 is internally provided with a communication passage 236 independent of liquid hole 237. Communication passage 236 allows second needle 233 and port 24 to be in communication with each other.

A cap 27 is attached to an end portion 26 of barrel attaching unit 21 near tip end 231*a* of first needle 231. Cap 27 has an annular form, and is provided at its center with a circular through-hole extending through cap 27 in a thickness direction thereof. This through hole has a diameter slightly larger than an outer diameter of the pipe portion formed of nozzle 14 and caulking member 122. Owing to the provision of the through hole, the pipe portion that is being inserted into barrel attaching unit 21 can be positioned to guide reliably first needle 231 and rubber cap 232 into the pipe portion, and cap 27 can hold barrel 1 when barrel 1 and connection tool 2 are connected together.

An elastic film 238 is held between end portion 26 and cap 27 fixed to end portion 26. Elastic film 238 is arranged over end portion 26 of barrel attaching unit 21 to cover it. A plurality of projections are formed at each of the surface of end portion 26 opposed to elastic film 238 and the surface of cap 27 opposed to elastic film 238. These projections fix and hold elastic film 238 between end portion 26 and cap 27. Elastic film 238 has a circular exposed portion that is externally exposed through the circular through-hole formed in cap 27.

Figure 4:
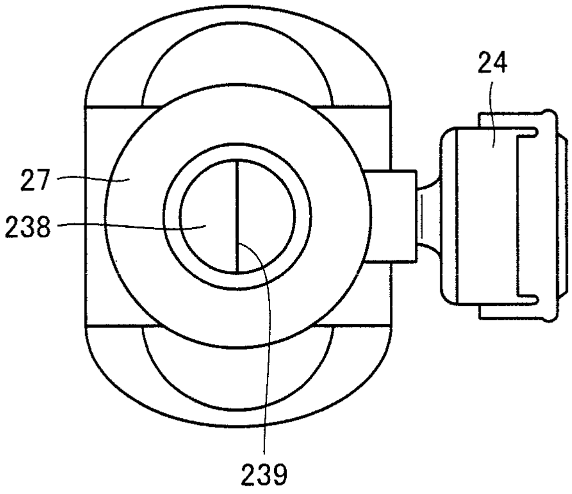
FIG. 4 is a plan of a connection tool viewed in a direction of an arrow IV in FIG. 2.

As shown in FIGS. 2 and 4, elastic film 238 has a slit opening 239, which has a straight from extending in a diametrical direction of the externally exposed circular portion of elastic film 238. Slit opening 239 extends between one and the other ends of the externally exposed circular portion of elastic film 238, and provides a boundary dividing the exposed portion into two semicircular portions.

Barrel 1 is a cylindrical member having a tip end, i.e., nozzle 14 and a base end, and are open at its opposite ends. Barrel 1 is normally made of glass or transparent plastic such as polypropylene, polyethylene, polymethylpentene or cyclic polyolefin. In barrel 1, nozzle 14 is sealed with sealing member 12 and its inner cavity on the base end side is sealed with gasket 11 inserted from the open base end. The space in barrel 1, which is defined by sealing member 12 and gasket 11, is filled with solvent S in advance. When the space is filled with solvent S, gasket 11 is preferably located to left a space on the base end side such that a certain amount of gas exceeding a nominal volume can be drawn thereinto when the drug solution is prepared and re-drawn. Solvent S is normally and appropriately a physiological saline or a glucose solution.

Normally, gasket 11 is slidably inserted from the open base end side of cylindrical barrel 1. Therefore, it takes a columnar form having a thickness that substantially prevents easy tilting of inserted gasket 11 as well as a size slightly smaller than a diameter of an inner peripheral wall of the barrel. Plunger 13 has a male screw at its tip end, and gasket 11 has a female screw at its inner cavity for receiving plunger 13. Gasket 11 and plunger 13 may have structures other than above general and, for example, may have rotatable structures disclosed in Japanese Patent Laying-Open Nos. 2002-272843 and 2008-307237.

Gasket 11 has annular ribs which are formed at its tip and base end portions, and are slightly larger in diameter than the inner peripheral wall of the barrel. This structure keeps the liquid-tightness between the inner peripheral wall of barrel 1 and gasket 11 when plunger 13 moves. A material of gasket 11 largely depends on compatibility with a drug stored in barrel 1, and is desirably natural rubber, butyl rubber, chlorinated butyl rubber, ethylene butadiene rubber, thermoplastic elastomer or the like.

Sealing member 12 is preferably formed of elastic member 121 and caulking member 122 as shown in FIG. 2. Membranes 121*a* and 121*b* forming elastic member 121 are thin membranes configured such that first needle 231 of connection tool 2 can readily penetrate through it and can be removed therefrom without loosing the liquid-tightness. Membrane 121*b* near opening 10, i.e., on the tip end side of the pipe portion formed of nozzle 14 and caulking member 122 may be made of any material provided that membrane 121*b* has a large restoring force for canceling elastic deformation. For example, membrane 121*b* may be made of an elastic material such as a rubber material (e.g., isoprene rubber or silicone rubber).

Membrane 121*a* on the base end side of the pipe portion, i.e., on the inner side of barrel 1 may be made of the same material as membrane 121*b*. However, when it is used in a storage container such as pre-filled syringe P, membrane 121*a* must be made of a material that does not dissolve in a drug solution. For example, membrane 121*a* may be made of a rubber material having a high chemical resistance such as butyl rubber.

Caulking member 122 must be made of a material having a relatively high modulus of elasticity so that it can be firmly and unremovably fitted or adhered into nozzle 14 at the tip end of barrel 1 and it can cooperate with elastic member 121 to keep the liquid-tightness. The material may be polypropylene, polycarbonate or aluminum.

First needle 231 is a syringe connection needle, and is covered with a rubber cap 232. First needle 231 must be made of a material that allows easy penetration through elastic member 121 of sealing member 12 attached to nozzle 14 and allows easy resealing of rubber cap 232 when connection tool 2 is removed from barrel 1. For example, first needle 231 is made of stainless steel, ABS (Acrylonitrile Butadiene Styrene) resin, SB (Styrene Butadiene) resin, polycarbonate or polystyrene.

Preferably, first needle 231 is worked and formed to locate tip end 231*a* on an axis or center of first needle 231 so that it can penetrate through a center of hemispherical projection 123, i.e., a portion of projection 123 that protrudes into barrel 1 and is remotest from opening 10. According to this structure, first needle 231 can preferably penetrate through membranes 121*a* and 121*b* with a circumferentially equal force so that a deformation of membranes 121*a* and 121*b* as well as leakage of the drug solution can be suppressed when first needle 213 penetrates therethrough. For example, first needle 231 is a bevel needle that is provided at tip end 231*a* with an obliquely cut opening that is cut obliquely to the extending direction of first needle 231. In this case, a bending work can be effected on tip end 231*a* to locate tip end 231*a* on the axis of first needle 231.

Preferably, rubber cap 232 has liquid-tightness so as to prevent leakage of the toxic drug when first needle 231 is stuck into or extracted from elastic member 121 of barrel 1. This kind of rubber cap 232 is preferably made of an elastic material such as natural rubber or synthetic rubber that has certain flexibility, a high restoration property, liquid-tightness and a high resealing property.

It is preferable that second needle 233 can readily penetrate through a rubber plug in the inlet of vial V, and is made of a material such as ABS resin, SB resin, polycarbonate or polystyrene. Preferably, second needle 233 has no pinhole at its axial center in order to prevent generation of an aerosol, which will float for a long period of time, when solvent S is directly jetted to a dry drug or a liquid surface in vial V. Liquid hole 237 for introducing solvent S into vial V has an opening at the surface of second needle 233, and this opening is preferably set in an appropriate position that can reduce a liquid remaining in vial V as far as possible when the prepared drug solution is re-drawn into barrel 1.

Elastic film 238 arranged at end portion 26 of barrel attaching unit 21 can be made of any elastic material provided that it can be restored when a load is released from elastic film 238. For example, elastic film 238 may be made of a rubber material such as isoprene rubber, butyl rubber or silicone rubber. Also, elastic film 238 can have any thickness provided that it is elastically restorable.

The form of slit opening 239 formed in elastic film 238 is not restricted to a form of a straight line, and it can have any form. For example, slit opening 239 may have a crosswise form. However, slit opening 239 of a straight-line form can be formed more easily than the others and thus is superior to the others.

Preferably, barrel attaching unit 21 is provided with a protruding piece or a lock mechanism for caulking barrel 1 slightly in order to prevent a disadvantage that a gap is formed at the peripheral edge of first needle 231 due to swaying during the operation and the toxic drug is dispersed therethrough.

Port 24 of connection tool 2 has an opening of communication passage 236 remote from second needle 233. When barrel 1, connection tool 2 and vial V are connected together with vial V located in the lower position, and plunger 13 is pushed to introduce solvent S in barrel 1 into vial V, the inner pressure applied to vial V discharges a gas from the system through communication passage 236. Communication passage 236 operates as a gas discharge passage. Aerosol filter 242 is arranged inside port 24 so that the drug solution may not leak from the system through port 24.

Aerosol filter 242 is made of water repellent resin such as polytetrafluoroethylene or ethylene-tetrafluoroethylene, or a hydrophobic material such as resin or fiber having a surface subjected to water repellent treatment. A pore diameter, a structure and a thickness of aerosol filter 242 are selected appropriately. However, an aerosol floating for a long period of time generally has a diameter in a range from about 10 nm to about 50 nm. In consideration of this as well as an electrostatic property and the like of the aerosol, a complex combination of a hydrophilic filter, a positively or negatively charged filter, an activated carbon and the like may be combined to form aerosol filter 242.

Figure 5:
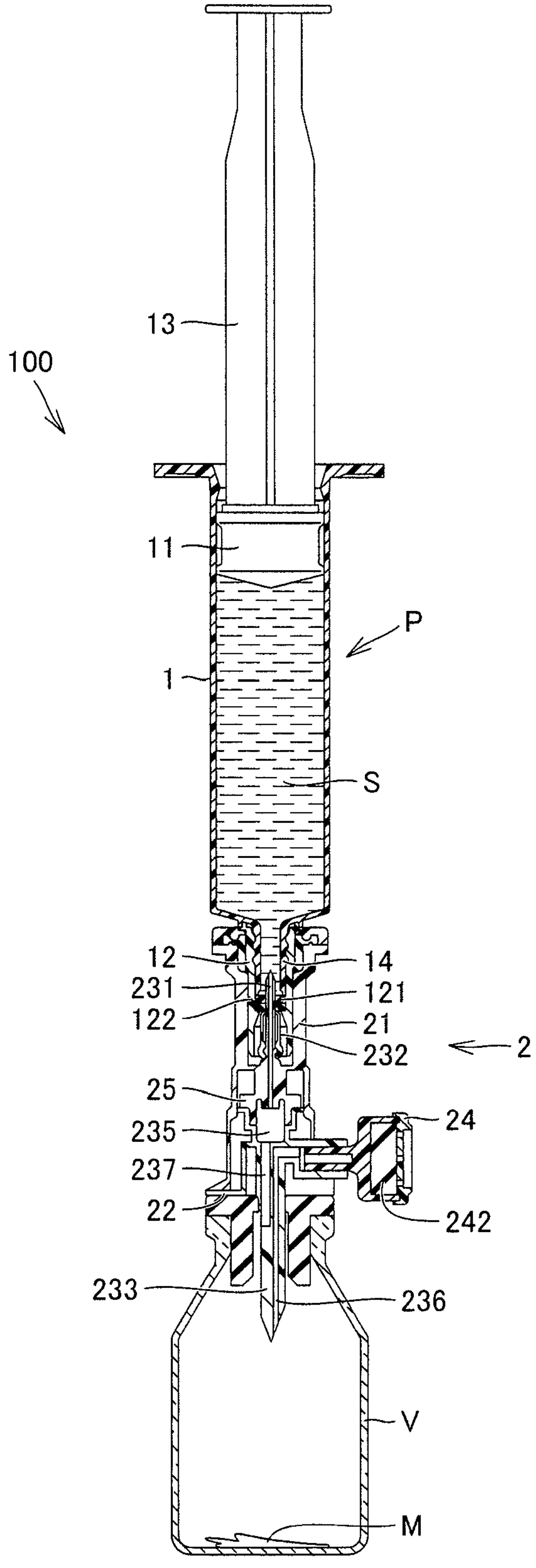
FIG. 5 is a cross section showing a state in which a pre-filled syringe is connected to a vial through the connection tool.
Figure 6:
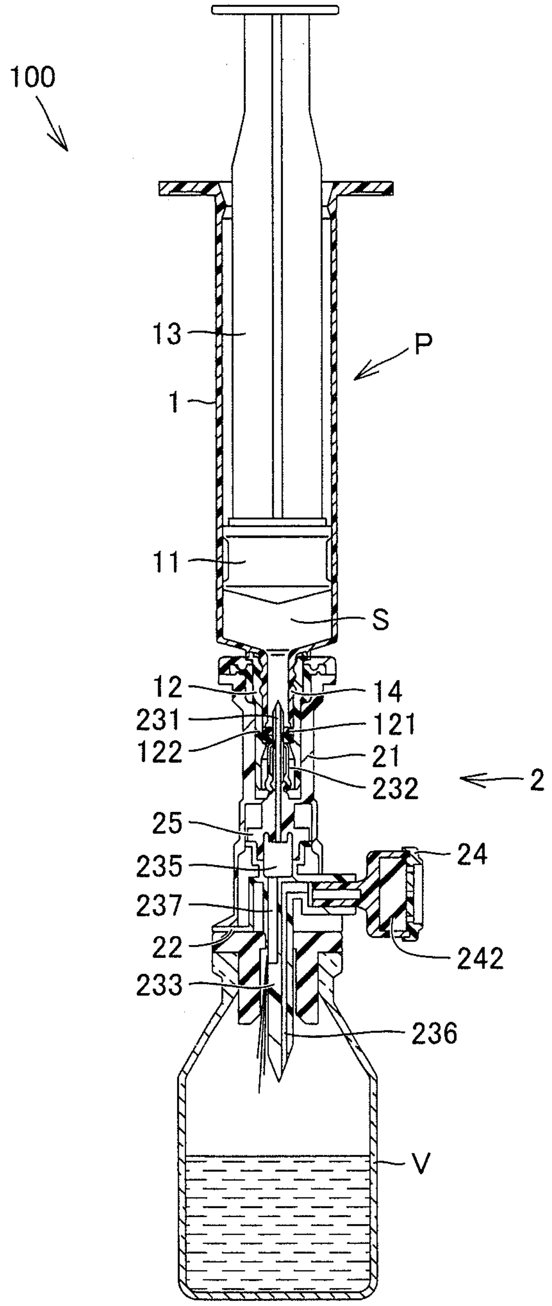
FIG. 6 is a cross section showing a state after a drug is prepared in the vial.

A manner of using drug solution transferring device 100 having the above structure will be described below. As shown in FIG. 5, vial V is attached to vial attaching unit 22 of connection tool 2 with the inlet side thereof being directed upward. Then, vial V of which bottom is located in the lower position is stably placed on a desk or the like, and barrel 1 of which tip end is directed downward is attached to barrel attaching unit 21 of connection tool 2.

Caulking member 122 attached to nozzle 14 at the end of barrel 1 has an outer diameter slightly smaller than an inner diameter of barrel attaching unit 21. Thus, the outer diameter of the pipe portion formed of nozzle 14 and caulking member 122 is smaller than the inner diameter of barrel attaching unit 21. Therefore, nozzle 14 and caulking member 122 can be inserted into barrel attaching unit 21 through slit opening 239 formed in elastic film 238.

When the pipe portion formed of nozzle 14 and caulking member 122 is inserted into barrel attaching unit 21, first needle 231 and rubber cap 232 accommodated in barrel attaching unit 21 enter space 16 in the pipe portion through opening 10. Connection tool 2 is connected to barrel 1 with first needle 231 (i.e., a part of connection tool 2) inserted into opening 10 of barrel 1. For example, the sizes of the pipe portion and barrel attaching unit 21 can be appropriately adjusted so that the inner peripheral surface of barrel attaching unit 21 is opposed to the outer peripheral surface of caulking member 122 with a minute space therebetween. By this adjustment, the pipe portion inserted into barrel attaching unit 21 can be positioned, and first needle 231 and rubber cap 232 can be reliably inserted into space 16 of the pipe portion.

When the pipe portion is further inserted into barrel attaching unit 21, elastic member 121 arranged at the tip end of nozzle 14 comes into contact with rubber cap 232. As the pipe portion moves relatively to barrel attaching unit 21, rubber cap 232 pushed by elastic member 121 elastically deforms to come into contact with tip end 231*a* of first needle 231. First needle 231 passes through rubber cap 232 and penetrates through membranes 121*a* and 121*b* forming elastic member 121.

When the pipe portion is inserted into barrel attaching unit 21, first needle 231 penetrates through projections 123 formed in membranes 121*a* and 121*b*. For this penetration, elastic member 121 and first needle 231 are appropriately arranged. For example, first needle 231 is arranged on the axis of barrel attaching unit 21, and projection 123 is arranged on the axis of the pipe portion. In this case, the pipe portion has the outer diameter slightly smaller than the inner diameter of barrel attaching unit 21. This configuration can provide the structure in which first needle 231 can reliably penetrate through projection 123.

When first needle 231 penetrates through membranes 121*a* and 121*b*, the inside and outside of barrel 1 are communicated with each other through liquid hole 234 formed inside first needle 231. Since first needle 231 penetrating through elastic member 121 protrudes into the inner space of barrel 1 that is liquid-tightly closed by barrel 1, gasket 11 and sealing member 12, solvent S filling barrel 1 can flow externally from barrel 1 through liquid hole 234 inside first needle 231. Since liquid hole 234 of first needle 231 allows the inside and outside of barrel 1 to be in communication with each other, solvent S can be transferred from barrel 1 to connection tool 2.

In the state where pre-filled syringe P and vial V are connected together through connection tool 2 as shown in FIG. 5, plunger 13 is slowly pushed downward with vial V located in the lower position. The movement of plunger 13 introduces solvent S from barrel 1 through liquid hole 234, communication space 235 and liquid hole 237 into vial V, and sprays it onto the inner wall of vial V. Concurrently, the gas in vial V is discharged through communication passage 236 formed in second needle 233 and port 24 to the outside of the system. In this manner, solvent S in barrel 1 is transferred into vial V. When vial V is shaken after the transfer of solvent S, dry drug M (see FIG. 5) in vial V is dissolved in solvent S to prepare the drug solution.

Figure 7:
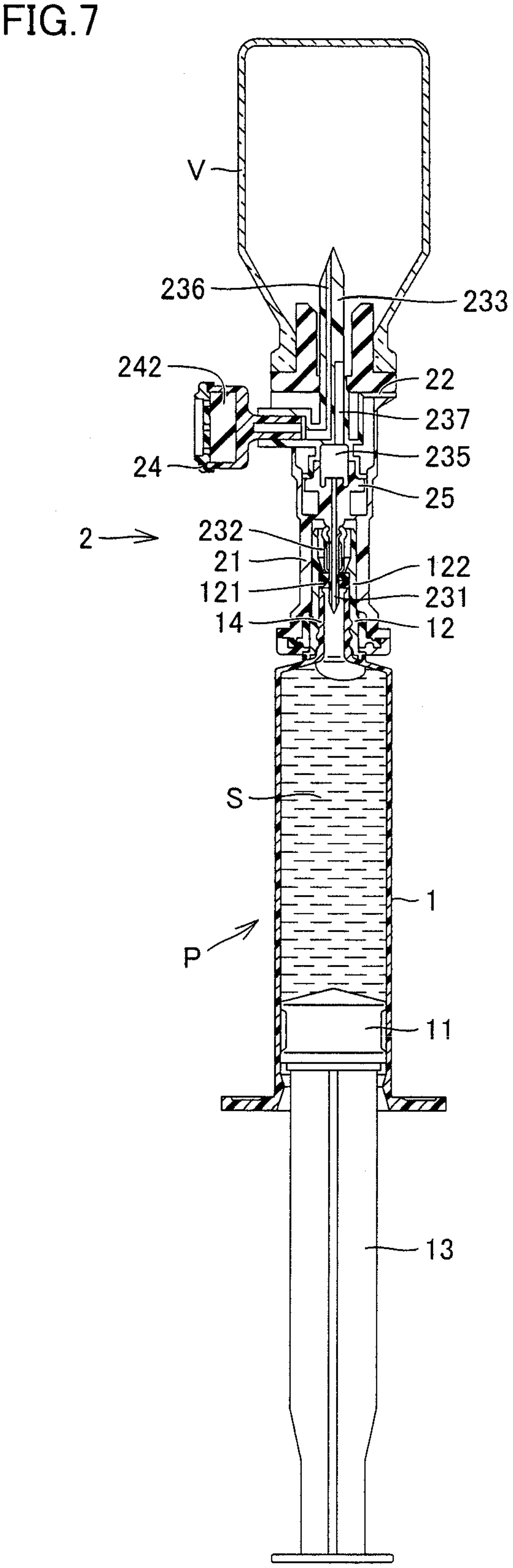
FIG. 7 is a cross section showing a state in which the prepared drug solution is re-drawn into the barrel.

After preparing the drug solution by dissolving in vial V, drug solution transferring device 100 is turned upside down as shown in FIG. 7 to locate vial V and pre-filled syringe P in the upper and lower sides, respectively. When plunger 13 is pulled downward in the above state, the drug solution is transferred from vial V into barrel 1 through liquid hole 234 in first needle 231, and a nominal amount of the drug solution is pulled and collected into barrel 1. The prepared drug solution is vial V is transferred into barrel 1. The drug solution is transferred between barrel 1 and connection tool 2 through liquid hole 234.

Figure 8:
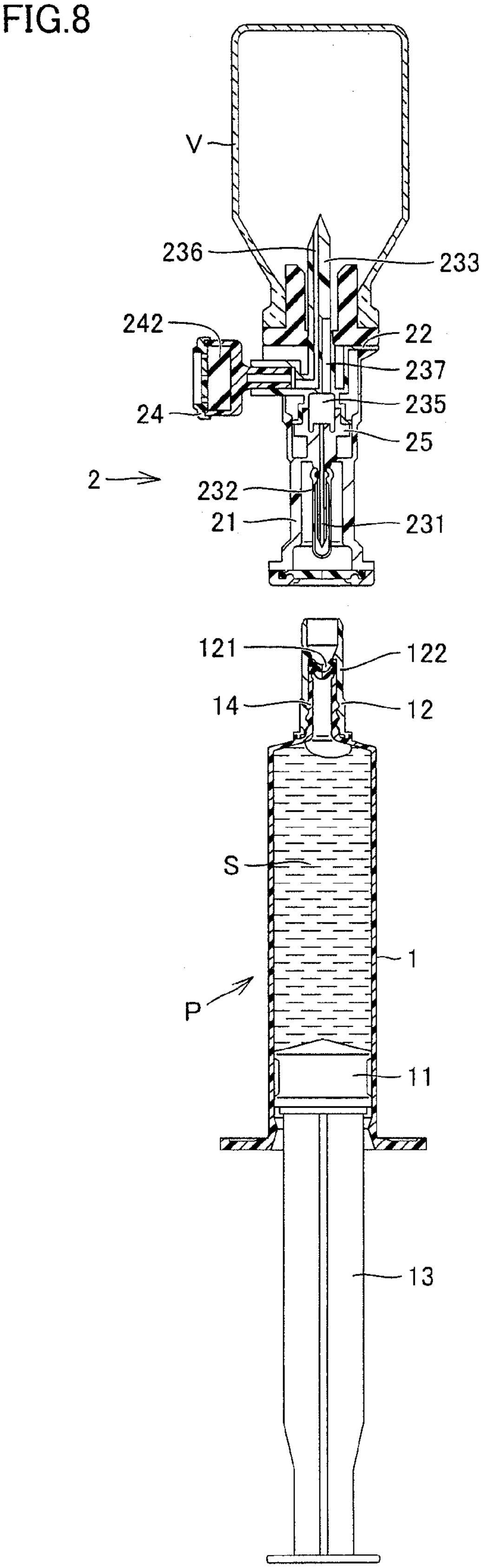
FIG. 8 is a cross section showing a state in which the barrel filled with the prepared drug solution is separated from the connection tool.

After the prepared drug solution is transferred from vial V to barrel 1 and barrel 1 is sealed, barrel 1 is removed from connection tool 2 as shown in FIG. 8. Then, a dedicated transfusion needle (not shown) is connected to the tip end of barrel 1 so that the drug solution in barrel 1 can be coinfused into a drip container as it is.

In the above state, it is preferable that gasket 11 is located rearward on the base end side of barrel 1 as compared with the position when barrel 1 is filled with solvent S. This configuration allows removal of pre-filled syringe P while keeping a reduced pressure in vial V. Therefore, even when the liquid leakage such as splash and the aerosol occur, these occur toward the inside of vial V so that dispersion of the drug solution to the surroundings can be avoided.

First needle 231 penetrating through elastic member 121 when barrel 1 was connected to connection tool 2 is pulled out from elastic member 121 when barrel 1 is separated from connection tool 2. Since the drug solution flowed from vial V through liquid hole 234 in first needle 231 into barrel 1, the drug solution has adhered onto tip end 231*a* of first needle 231. When first needle 231 is pulled out from elastic member 121, first needle 231 slides on elastic member 121 while keeping an intimate contact between its outer peripheral surface and elastic member 121. First needle 231 moves relatively to elastic member 121 with a pressing force being applied to its periphery by elastic member 121. The relative movement of first needle 231 causes an operation of squeezing or rubbing first needle 231 by elastic member 121.

When first needle 231 is pulled out from elastic member 121, elastic member 121 squeezing or rubbing first needle 231 removes the drug solution adhered onto the surface of first needle 231. More specifically, membrane 121*b* near opening 10 rubs off the adhered drug solution from first needle 231, and the drug solution thus removed is caught between membranes 121*a* and 121*b*. Membrane 121*b* has projection 123 protruding into barrel 1, and first needle 231 penetrates through projection 123 so that membrane 121*b* exhibits the squeezing or rubbing function. Since the plurality of membranes 121*a* and 121*b* are overlaid together to form elastic member 121, the drug solution can be caught between the plurality of membranes 121*a* and 121*b*.

In drug solution transferring device 100 according to the first embodiment, as described above, elastic member 121 can remove the drug solution adhered onto first needle 231 so that drug solution transferring device 100 can suppress remaining of the drug solution on the surface of first needle 231. The drug solution rubbed off by elastic member 121 from first needle 231 is caught between the plurality of membranes 121*a* and 121*b* so that drug solution transferring device 100 can suppress the dispersion of the drug solution removed from first needle 231 to the outside of the system from elastic member 121. Therefore, when the toxic drug solution is to be transferred, such a state can be suppressed that the drug solution changes into an aerosol to splash and spread to a surrounding environment. Consequently, such a situation can be suppressed that workers such as medical staffs and patients using the drug solution are exposed to the aerosol of a high drug concentration and their health is impaired. Therefore, the embodiment can provide the easy-to-handle and safe drug solution transferring device 100.

When membranes 121*a* and 121*b* are made of a rubber material having a large restoring force, these exhibit the rubbing function described above so that the drug solution can be rubbed and removed from first needle 231. However, if membrane 121*b* had an extremely small thickness, the rubbing function of membrane 121*b* would probably be low. Therefore, it is desired to employ membrane 121*b* having a sufficient thickness for removing the drug solution from first needle 231.

Projections 123 formed in membranes 121*a* and 121*b* have the hemispherical form. Projection 123 can have an arbitrary form provided that it protrudes toward the inside of barrel 1, and may have a conical or pyramidal form. However, projection 123 of the first embodiment, i.e., dome-shaped projection 123 is more preferable because it can stably exhibit the function of rubbing off the drug solution from the surface of first needle 231 by membrane 121*b* even when first needle 231 penetrates through a position deviated from the center of projection 123.

Further, drug solution transferring device 100 of the first embodiment is provided with elastic film 238 covering end portion 26 of barrel attaching unit 21. Nozzle 14 and caulking member 122 on the end of barrel 1 extends into barrel attaching unit 21 through slit opening 239 formed in elastic film 238. Even if the toxic drug solution remaining on the outer surface of first needle 231 adheres to rubber cap 232 when barrel 1 is being removed from connection tool 2, the above structure can suppress the dispersion of the drug solution adhered onto rubber cap 232 to the outside of the system because elastic film 238 covers the inner space of barrel attaching unit 21.

Therefore, the first embodiment can further suppress the external dispersion of the aerosol of drug solution.

Second Embodiment

Figure 9:
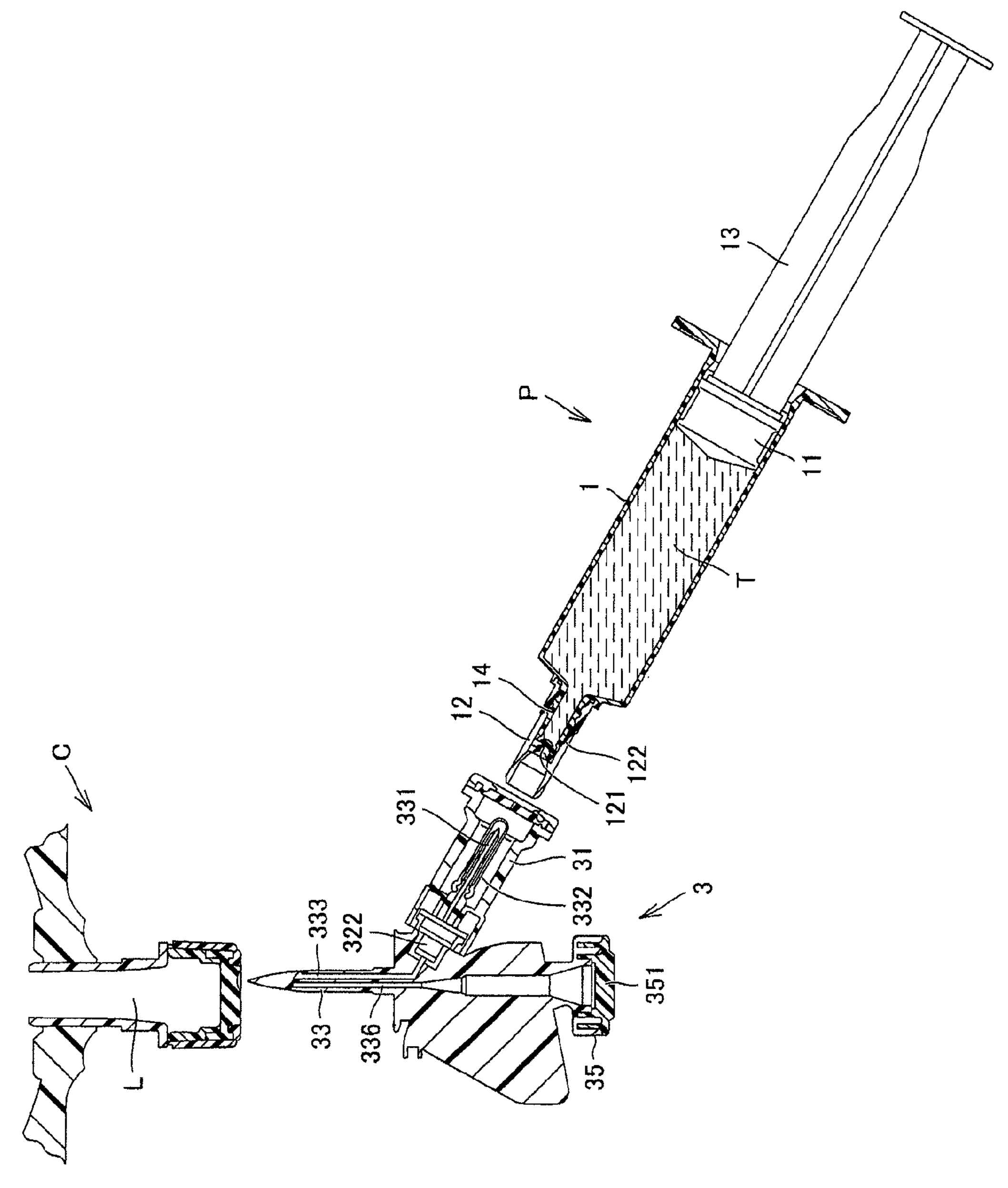
FIG. 9 is a cross section showing a structure of a drug solution transferring device according to a second embodiment of the invention.

As shown in FIG. 9, a drug solution transferring device according to a second embodiment includes a drug solution-filled syringe P filled with a toxic drug solution T and a connection tool 3 connected to drug solution-filled syringe P. Connection tool 3 is attached to an infusion container C filled with a drug solution L and drug solution-filled syringe P for connecting them together. Since drug solution-filled syringe P and infusion container C are in communication with each other through connection tool 3, drug solution L in infusion container C and toxic drug solution T are mixed and dissolved together.

Drug solution-filled syringe P has the same structure as the pre-filled syringe in the first embodiment, and therefore description thereof is not repeated. Drug solution-filled syringe P filled with toxic drug solution T may be a pre-filled syringe that is filled in advance with toxic drug solution T or a syringe filled with a drug solution prepared by drug solution transferring device 100 of the first embodiment.

Figure 10:
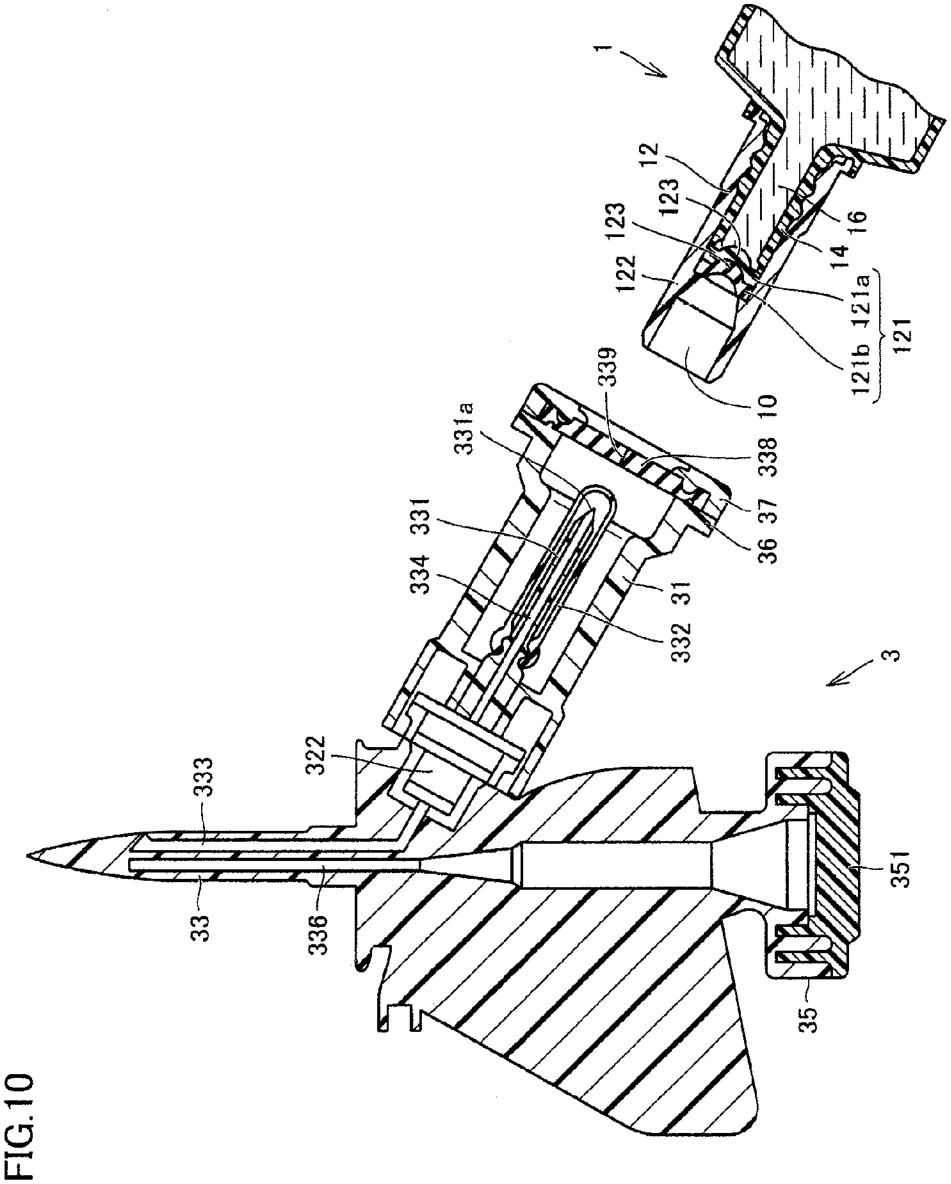
FIG. 10 is a fragmentary cross section showing, on an enlarge scale, the drug solution transferring device shown in FIG. 9.

As shown in FIG. 10, connection tool 3 has a central axis extending in the direction of penetration through a plug of infusion container C, is provided at the upper and lower ends with a second needle 33 and an output port 35, respectively, and has a cylindrical barrel attaching unit 31 protruding obliquely downward. Barrel attaching unit 31 has a first needle 331 that is located in the coaxial position for penetrating through elastic member 121 of sealing member 12 at the end of barrel 1 when drug solution-filled syringe P is attached to barrel attaching unit 31. First needle 331 is covered with a covering unit, i.e., a rubber cap 332. First needle 331 has a liquid hole 334, which opens at a tip end 331*a* of first needle 331.

A cap 37 is attached to an end portion 36 of barrel attaching unit 31 near tip end 331*a* of first needle 331. An elastic film 338 is held between end portion 36 and a cap unit 37 fixed to end portion 36. Elastic film 338 is arranged on end portion 36 of barrel attaching unit 31, and covers end portion 36. Elastic film 338 is provided with a slit opening 339. Slit opening 339 has a form of straight line extending in a diametrical direction of an externally exposed circular portion of elastic film 338.

Second needle 33 is provided with a liquid hole 333 and a communication passage 336 independent of each other. Liquid hole 333 is in communication with liquid hole 334 of first needle 331. Communication passage 336 is in communication with output port 35. A closing member 351 through which a bottle needle of an infusion line will penetrate is arranged at the end of output port 35.

A liquid valve 322 that can bidirectionally open in response to a predetermined pressure or more is arranged on the base end side of barrel attaching unit 31. When liquid holes 334 and 333 of first and second needles 331 and 33 are communicated with each other to transfer toxic drug solution T from barrel 1 to infusion container C by a pressure, and this pressure opens liquid valve 322. Liquid valve 322 opens only when the liquid pressure is equal to or higher than a predetermined pressure. Therefore, when the infusion line is connected to output port 35 of connection tool 3 to transfer the drug solution from infusion container C to the infusion line, liquid valve 322 prevents returning of the drug solution into barrel 1. Liquid valve 322 described above may be replaced with a one-way valve that allows a flow of liquid from liquid hole 334 to liquid hole 333 and prohibits a flow in the reverse direction so that toxic drug solution T can be irreversibly transferred from barrel 1 to infusion container C.

First needle 331 is covered with rubber cap 332 to ensure the liquid tightness for preventing leakage of the toxic drug when the needle is stuck into or extracted from elastic member 121 of barrel 1. The material of first needle 331 is required to allow easy penetration through elastic member 121 of sealing member 12 attached to nozzle 14 and to allow easy resealing by rubber cap 332 when barrel 1 is removed. For example, first needle 331 may be made of stainless steel, ABS resin, SB resin, polycarbonate or polystyrene.

Rubber cap 332 is preferably made of an elastic material such as natural rubber or synthetic rubber that has certain flexibility and a high restoring property as well as high liquid-tightness and a high sealing property.

Preferably, second needle 33 is configured to allow easy sticking through the plug of infusion container C, and is made of ABS resin, SB resin, polycarbonate or polystyrene. Preferably, the openings of liquid hole 333 and communication passage 336 formed on the surface of second needle 33 are appropriately spaced from each other for promoting dilution of toxic drug solution T in infusion container C. For example, it is preferable that the needle hole is not formed on the central axis of second needle 33.

Preferably, barrel attaching unit 31 is provided with a protruding piece or a lock mechanism for slightly caulking barrel 1 after attaching barrel 1 so as to prevent such a situation that a space is formed around first needle 331 due to sway during the operation and thereby the toxic drug disperses therethrough. Elastic film 338 arranged at end portion 36 of barrel attaching unit 31 is made of an elastic material, which is not restricted provided that it can restore when a load is released from elastic film 338. For example, elastic film 338 may be made of a rubber material such as isoprene rubber, butyl rubber or silicone rubber.

Output port 35 of connection tool 3 is in communication with communication passage 336 formed in second needle 33, and is closed by a closing member 351 such that output port 35 can open to the infusion line connected thereto. Closing member 351 is normally a thin film having elasticity so that it allows sticking of the bottle needle of the infusion line, does not allow easy disengagement of the bottle needle in the sticking position and does not impair the liquid-tightness. A material of closing member 351 satisfying the above performance is determined in view of compatibility with a drug solution in contact with it, and is appropriately selected from among natural rubber, butyl rubber, chlorinated butyl rubber, styrene butadiene rubber, thermoplastic elastomer and the like. The opening of output port 35 preferably has a cylindrical form having an inner diameter slightly smaller than the diameter of the bottle needle for assisting holding of the bottle needle of the infusion line.

Similarly to drug solution transferring device 100 of the first embodiment, the drug solution transferring device having the above structures can remove the drug solution adhered to first needle 331 by elastic member 121, and therefore can suppress remaining of the drug solution on the surface of first needle 331. The drug solution rubbed off from first needle 331 by elastic member 121 is caught between the plurality of membranes 121*a* and 121*b* so that such a situation can be suppressed that the drug solution removed from first needle 331 disperses through elastic member 121 to the outside of the system. Therefore, it is possible to suppress such a situation that the toxic drug solution takes an aerosol form and disperses to the surrounding environment during transference of the drug solution.

Further, end portion 36 of barrel attaching unit 31 is covered with elastic film 338. Nozzle 14 and caulking member 122 at the tip end of barrel 1 are inserted into barrel attaching unit 21 through slit opening 339 formed in elastic film 338. According to this configuration, elastic film 338 covers the inner space of barrel attaching unit 31. Therefore, even in the case where the toxic drug solution remaining on the outer surface of first needle 331 adheres to rubber cap 332 when barrel 1 is removed from connection tool 2, it is possible to suppress dispersion of the drug solution adhering to rubber cap 332 to the outside of the system because elastic film 338 covers the inner space of barrel attaching unit 31. This can further suppress the external dispersion of the aerosol of the drug solution.

The first and second embodiments have been described in connection with the examples in which elastic member 121 of barrel 1 includes two membranes 121*a* and 121*b*. This structure is not restrictive. It is merely required that elastic member 121 includes two or more membranes overlaid together, because it is employed for rubbing off the drug solution adhering to the first needle by the membrane near opening 10 of barrel 1, catching the rubbed-off drug solution between the plurality of membranes and thereby suppressing the dispersion of the drug solution. As the number of membranes increases, elastic member 121 can remove the drug solution from the first needle more effectively. However, as the number of membranes increases, the difficulty in sticking the first needle through elastic member 121 increases. Therefore, it is desirable to set appropriately the number of the membranes in view of the drug solution removing performance of elastic member 121 and the degree of easiness with which the first needle can be stuck through elastic member 121.

Connection tool 2 of the first embodiment connects pre-filled syringe P to vial V, and connection tool 3 of the second embodiment connects drug solution-filled syringe P to infusion line (not shown). However, the drug solution transferring device according to the invention is not restricted to the above example. The drug solution transferring device according to the invention can be used for transferring any liquid of which external leakage is to be suppressed.

For example, in addition to dangerous drug such as anti-cancer drug, the drug solution transferring device of the invention can be used for transferring a liquid containing pathogenic bacteria, bacteria to be prevented from having resistance, or the like. Specifically, the drug solution transferring device according to the invention can be appropriately used, e.g., for transferring a drug solution from a pre-filled syringe to a drug bag, for transferring an infusion from an infusion line to an empty syringe for sampling, for transferring a liquid specimen containing pathogenic bacteria from a specimen collecting tool to an inspection kit. Also, the drug solution transferring device according to the invention can be used for transferring a dangerous solvent such as trichloroethylene or a solution containing an endocrine-disrupting substance.

Although the present invention has been described and illustrated in detail, it is clearly understood that the same is by way of illustration and example only and is not to be taken by way of limitation, the scope of the present invention being interpreted by the terms of the appended claims.

What is claimed is:

1. A drug solution transferring device comprising:

a drug solution container provided with an opening; and a connection tool for connection to said drug solution container, wherein said drug solution container includes an elastic member for closing said opening, said elastic member is formed of a plurality of membranes overlaid together, said membrane has a projection projecting into said drug solution container, said connection tool includes a needle having a sharp tip end, said needle has a liquid hole extending in an extending direction of said needle, and when said needle penetrates through said projection of said membrane, an inside and an outside of said drug solution container are in communication with each other through said liquid hole to allow transference of the drug solution between said drug solution container and said connection tool, and wherein the plurality of membranes are disposed to be in direct contact with each other without a space formed therebetween before use of the drug solution container, and are independent of and not bonded with each other, and the elastic member is configured to catch drug solution between the plurality of membranes when the needle is removed from the drug solution container.

2. The drug solution transferring device according to claim 1, wherein said projection has a hemispherical form.

3. The drug solution transferring device according to claim 1, wherein said connection tool includes: an elastically deformable covering unit covering said needle, a hollow cylindrical portion accommodating said needle and said covering unit, and an elastic film arranged at an end portion of said hollow cylindrical portion near said tip end of said needle and covering said end portion; and said elastic film has a slit opening.

4. The drug solution transferring device according to claim 3, wherein said drug solution container includes a pipe portion projecting toward an outside of said drug solution container, said elastic member is arranged to close a hollow in said pipe portion, said pipe portion has an outer diameter smaller than an inner diameter of said hollow cylindrical portion for allowing insertion of said pipe portion through said slit opening into said hollow cylindrical portion, and said needle is stuck into said membrane by inserting said pipe portion into said cylindrical portion.

5. The drug solution transferring device according to claim 1, wherein the plurality of membranes conform in shape to each other and protrude toward inside of the drug solution container to form a spherically-curved surface to be in contact with drug solution contained within the drug solution container.

6. The drug solution transferring device according to claim 1, wherein the drug solution container includes a caulking member unremovably coupled to an outer periphery of the opening of the drug solution container, the caulking member includes a step formed on an inner periphery of the caulking member, and the plurality of the membranes are clamped between the step and the opening of the drug solution container to seal the opening of the drug solution container.

7. The drug solution transferring device according to claim 1, wherein when the needle is removed from the drug solution container, at least one of the plurality of membranes is configured to rub the needle, and have a restoring force to remove drug solution from the needle and catch drug solution between the plurality of membranes.

* * * * *